(12) United States Patent
Hogue

(10) Patent No.: US 8,702,177 B1
(45) Date of Patent: Apr. 22, 2014

(54) SHOULDER AND WAIST HARNESS FOR USE WITH A WHEELCHAIR

(76) Inventor: Sherry L. Hogue, North Richland Hills, TX (US)

(*) Notice: Subject to any disclaimer, the term of this patent is extended or adjusted under 35 U.S.C. 154(b) by 112 days.

(21) Appl. No.: 13/443,038

(22) Filed: Apr. 10, 2012

(51) Int. Cl.
A47C 31/00 (2006.01)

(52) U.S. Cl.
USPC .......................... 297/484; 297/485

(58) Field of Classification Search
USPC ............. 297/483, 484, 485, DIG. 4, 464, 465
See application file for complete search history.

(56) References Cited

U.S. PATENT DOCUMENTS

| 1,288,170 | A | * | 12/1918 | Pick | 297/484 |
| 3,954,280 | A | * | 5/1976 | Roberts et al. | 297/484 |
| 4,050,737 | A | * | 9/1977 | Jordan | 297/465 |
| 4,205,670 | A | * | 6/1980 | Owens | 297/485 |
| 4,226,474 | A | * | 10/1980 | Rupert et al. | 297/484 |
| 4,834,460 | A | * | 5/1989 | Herwig | 297/485 |
| 4,861,109 | A | * | 8/1989 | Leach | 297/485 |
| 4,871,210 | A | * | 10/1989 | Alexander et al. | 297/485 |
| 4,898,185 | A | * | 2/1990 | Fuller | 297/485 |
| 4,927,211 | A | * | 5/1990 | Bolcerek | 297/465 |
| 4,966,392 | A | * | 10/1990 | Featon et al. | 297/DIG. 4 |
| 5,325,818 | A | * | 7/1994 | Leach | 119/770 |
| 5,397,171 | A | * | 3/1995 | Leach | 297/484 |
| 5,522,404 | A | * | 6/1996 | Williams | 297/483 |
| 5,628,548 | A | * | 5/1997 | Lacoste | 297/484 |
| 5,664,844 | A | * | 9/1997 | Greene | 297/485 |
| 5,816,662 | A | * | 10/1998 | Rumburg | 297/484 |
| 6,626,131 | B2 | * | 9/2003 | Moulton, III | 119/770 |
| 7,073,866 | B1 | * | 7/2006 | Berdahl | 297/485 |
| 7,628,157 | B2 | * | 12/2009 | Kosh | 128/874 |
| D608,950 | S | * | 1/2010 | Kelly et al. | D29/101.3 |
| D668,393 | S | * | 10/2012 | Hogbin | D29/101.1 |
| 8,342,608 | B1 | * | 1/2013 | Cook | 297/485 |

* cited by examiner

Primary Examiner — Jose V Chen
(74) Attorney, Agent, or Firm — Kyle A. Fletcher, Esq.

(57) ABSTRACT

The shoulder and waist harness for use with a wheelchair includes a horizontal belt that extends around both the torso of an occupant and a seat back of a wheelchair. A pair of shoulder straps attaches to a rear portion of the horizontal belt, and extend vertically up and over the seat back as well as shoulders of an occupant. A front end of each shoulder strap secures to a portion comprising a front cover located at a front portion of the restraining harness. The front cover being comprised of a front member and a rear member that include a nylon hook or loop strip so as to secure to one another. A shoulder strap and corresponding side of the horizontal belt is affixed to the front member, and an opposing shoulder strap and corresponding side are affixed to the rear member.

12 Claims, 3 Drawing Sheets

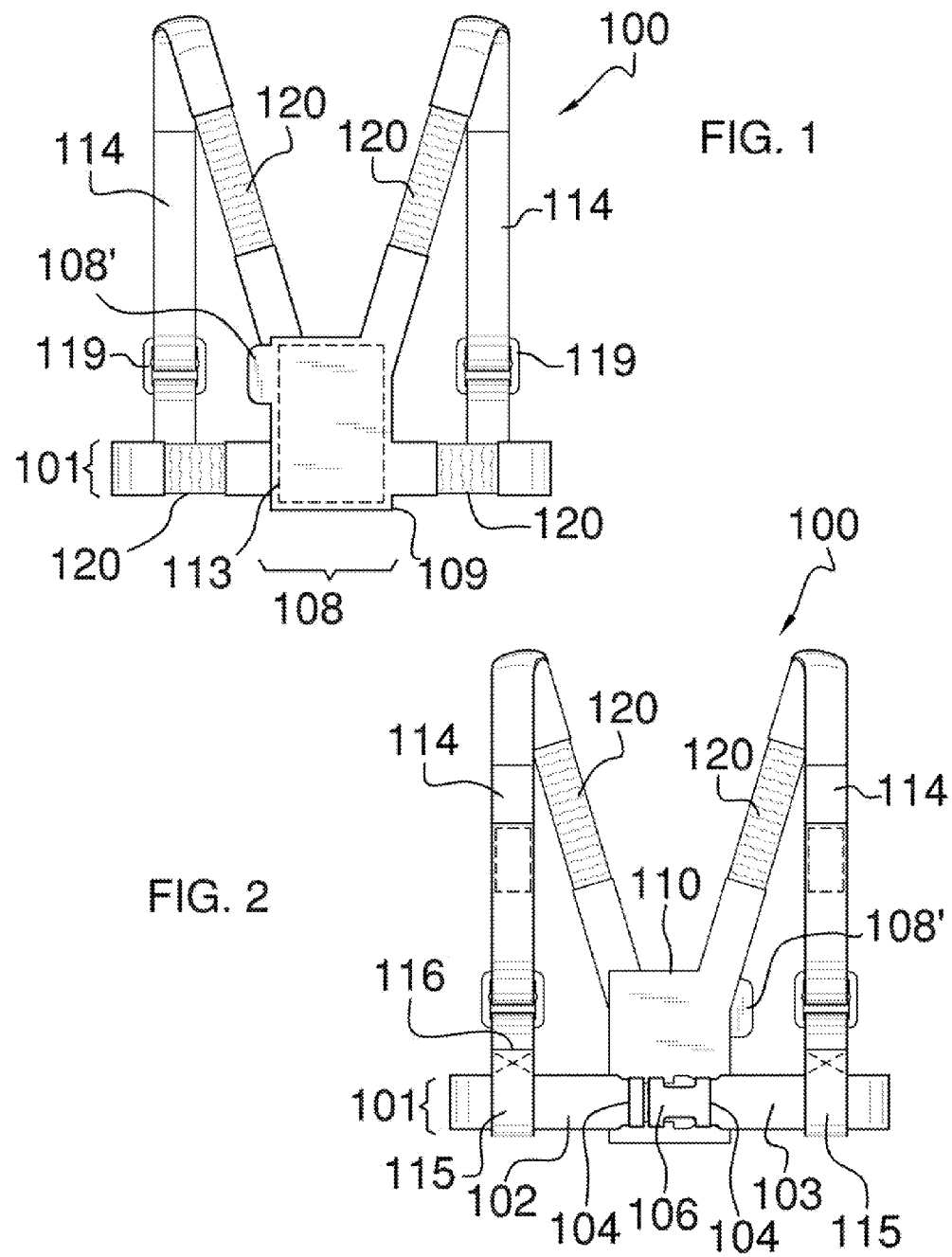

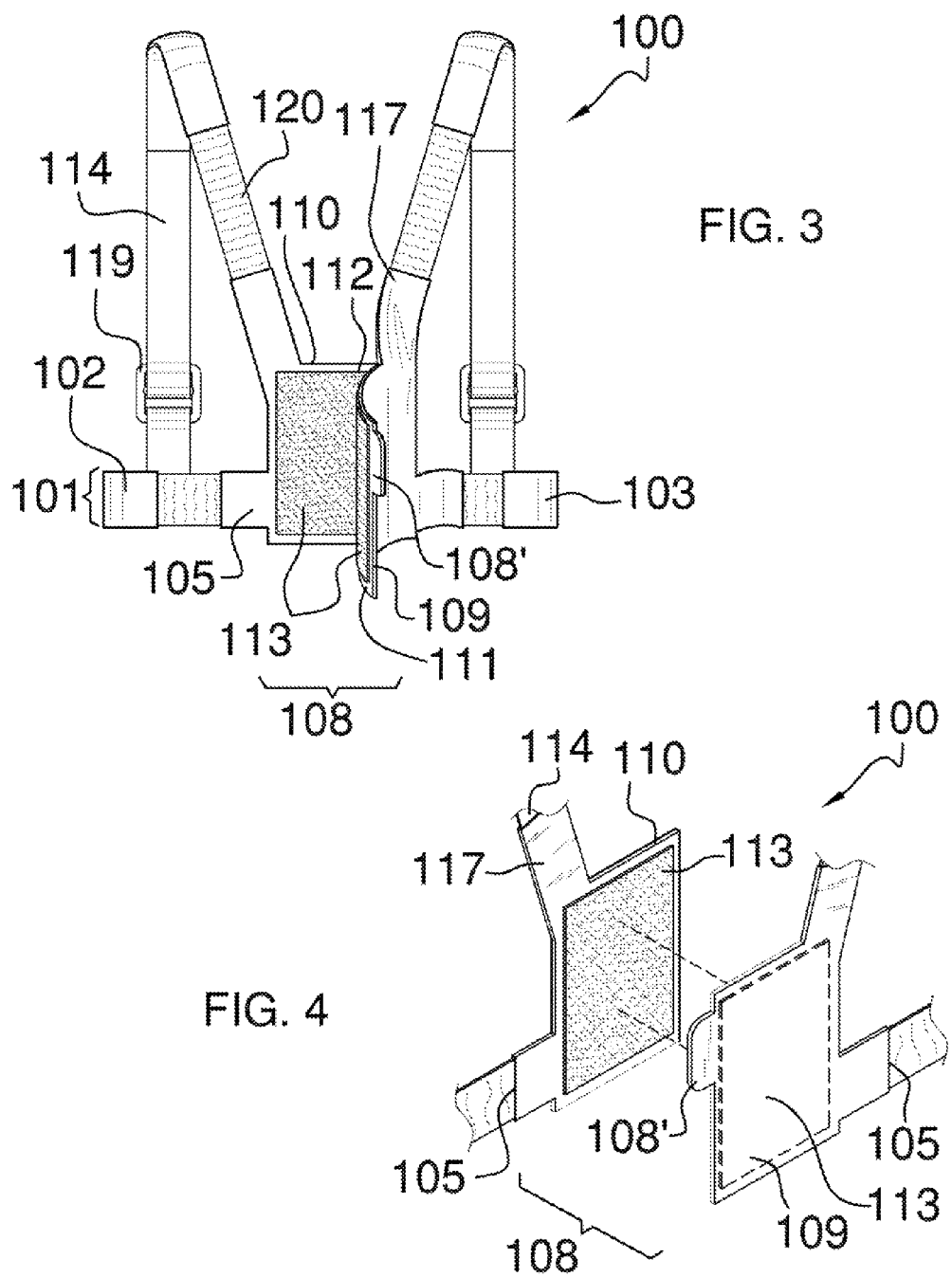

SHOULDER AND WAIST HARNESS FOR USE WITH A WHEELCHAIR

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of wheelchairs, more specifically, a harness for securing an occupant's torso to the seat back portion of a wheelchair.

Traditionally, a wheelchair is a wheeled seat, which does not prevent an occupant from falling out of said, wheel chair when in use. This is a problem where the occupant is mentally or physically handicapped, and may otherwise fall from the wheelchair.

What is needed is a harness system that secures the torso portion of an occupant to the seat back portion Of the wheelchair in an effort to prevent unintended falling from the wheelchair.

B. Discussion of the Prior Art

As will be discussed immediately below, no prior art shoulders and torso to the seat back of a wheelchair; wherein the safety harness includes a horizontal belt that encircles both the torso and the seat back of the wheelchair; wherein a pair of shoulder straps extend vertically from a rear of the horizontal belt and extend up and over the seatback of the wheelchair and over shoulders of the occupant where a front end of each shoulder straps is secured to a portion comprising a front cover thereby securing the torso of the occupant to the wheelchair; wherein the front cover secures the front ends of the shoulder strap as well as front ends the horizontal belt; wherein the front cover includes a front member a rear member that each include a nylon hook or loop strip so as to secure the front member to the rear member; wherein the front member is affixed to a shoulder strap and a corresponding side of the horizontal belt, whereas the rear member is affixed to an opposing shoulder strap and a corresponding side of the horizontal belt.

The Greene Patent (U.S. Pat. No. 5,664,844) discloses a harness system for securing a child or mentally or physically impaired adult to a wheelchair, or similar seating device, which includes a Velcro fastener. However, the harness system does not encircle the torse and seat back of a wheelchair and from which shoulder straps extend to encircle each shoulder, respectively, and in order to restrain a torso of an occupant to the seat back and to the wheelchair.

The Featon et al. Patent (U.S. Pat. No. 4,966,392) discloses a wheelchair with a harness for restraining an occupant. However, the harness is directed to securing a wheelchair and it's occupant to a floor surface of a vehicle.

The Rupert et al. Patent (U.S. Pat. No. 4,226,474) discloses a safety vest that is worn by a person for holding a person in a seat. However, the safety vest uses rings to attach straps with clips that extend from a surface or a seat to secure the vest to the respective object, as opposed to a safety harness that encircles a seat back of a wheelchair and a torso of an end user.

The Berdahl Patent (U.S. Pat. No. 7,073,866) discloses a fully adjustable universal safety harness for restraining small children to secure said small children in various chairs. However, the safety harness features an adjustable strap that encircles a seat to secure the harness thereto, as opposed to a single harness system that loops around both the torso and seat back, and from which shoulder straps extend to wrap over shoulders of and secure an occupant thereto.

The Williams Patent (U.S. Pat. No. 5,522,404) discloses an adjustable safety and assistance harness that is mountable to a chair or a wheelchair. However, the adjustable safety harness does not fully encircle the seat back and the torso of an occupant, but rather engages handlebars of the wheelchair.

The Jordan Patent (U.S. Pat. No. 4,050,737) discloses a support harness for a child that is used for maintaining a sitting position in a chair. However, the support harness extends underneath the occupant by traversing through the legs.

The Collins Patent (U.S. Pat. No. 5,042,878) discloses an invalid chair or wheelchair restraint. However, the restraint traverses under and in between the legs of the occupant, and does not include shoulder straps that secure the upper torso to the seat back.

The Bolcerek Patent (U.S. Pat. No. 4,927,211) discloses a safety harness with a chest pad, back pad, and shoulder pads. However, the safety harness does not rely upon a horizontal loop to encircle both the torso and seat back of a wheel chair, and from which shoulder straps extend there from.

The Leach Patent (U.S. Pat. No. 5,397,171) discloses an apparatus worn by a patent seated in a wheelchair. However, the apparatus traverses under and behind the seat back to engage the lower frame of the wheelchair.

The Kelley et al. Patent (U.S. Pat. No. Des. 608,950) illustrates a design for a child safety harness for a wheelchair. However, the child safety harness is used to secure a child onto the lap of an adult occupant who is also seated in a wheelchair. Furthermore, the child safety harness relies upon cross-crossing straps to the back of the child, and is not capable of securing the upper torso of an adult occupant to the wheelchair.

While the above-described devices fulfill their respective and particular objects and requirements, they do not describe a safety harness for a wheelchair that secures the shoulders and torso to the seat back of a wheelchair; wherein the safety harness includes a horizontal belt that encircles both the torso and the seat back of the wheelchair; wherein a pair of shoulder straps extend vertically from a rear of the horizontal belt and extend up and over the seatback of the wheelchair and over shoulders of the occupant where a front end of each shoulder straps is secured to a portion comprising a front cover thereby securing the torso of the occupant to the wheelchair; wherein the front cover secures the front ends of the shoulder strap as well as front ends the horizontal belt; wherein the front cover includes a front member a rear member that each include a nylon hook or loop strip so as to secure the front member to the rear member; wherein the front member is affixed to a shoulder strap and a corresponding side of the horizontal belt, whereas the rear member is affixed to an opposing shoulder strap and a corresponding side of the horizontal belt. In this regard, the shoulder and waist restraining harness for use with a wheelchair departs from the conventional concepts and designs of the prior art.

SUMMARY OF THE INVENTION

The shoulder and waist harness for use with a wheelchair includes a horizontal belt that extends around both the torso of an occupant and a seat back of a wheelchair. A pair of shoulder straps attaches to a rear portion of the horizontal belt, and extend vertically up and over the seat back as well as shoulders of an occupant. A front end of each shoulder strap secures to a portion comprising a front cover located at a front portion of the restraining harness. The front cover being comprised of a front member and a rear member that include nylon hook or loop strip so as to secure to one another. A shoulder strap and corresponding side of the horizontal belt is affixed to the front member, and an opposing shoulder strap and corresponding side are affixed to the rear member.

It is an object of the invention to provide a harness system that secures a torso of an occupant to a seat back of a wheelchair by simply employing a horizontal belt that extends around both the torso and seat back, and a pair of shoulder straps that extend vertically up and over both the shoulders and seat back.

A further object of the invention is to provide a front cover that enables front ends of the horizontal belt as well as front ends of the shoulder straps to be secured centrally at the front cover.

A further object of the invention is to provide both the front member and the rear member of the front cover with nylon hook and loop stripping so as to enable adjustability of the safety harness for differently sized occupants and/or wheelchairs.

Another object of the invention is to affix the front member to one of the shoulder straps and a corresponding side of the horizontal belt while the rear member is affixed to an opposing shoulder strap and corresponding side of the horizontal belt.

A further object of the invention is to provide a safety harness that has elastic stripping built into the horizontal belt to provide for further adjustability and comfort.

Another object of the invention is to provide additional nylon hook or loop stripping upon the shoulder straps, which engages a rear surface of the seat back of the wheelchair in order to further secure itself thereon.

Another object of the invention is to include a buckle to the rear of the horizontal belt, which can be connected after applying the harness over the shoulders of the occupant.

These together with additional objects, features and advantages of the shoulder and waist harness for use with a wheelchair will be readily apparent to those of ordinary skill in the art upon reading the following detailed description of presently preferred, but nonetheless illustrative, embodiments of the shoulder and waist harness for use with a wheelchair when taken in conjunction with the accompanying drawings.

In this respect, before explaining the current embodiments of the shoulder and waist harness for use with a wheelchair in detail, it is to be understood that the shoulder and waist harness for use with a wheelchair is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the shoulder and waist harness for use with a wheelchair.

It is therefore important that the claims be regarded as including such equivalent construction insofar as they do not depart from the spirit and scope of the shoulder and waist harness for use with a wheelchair. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention:

In the drawings:

FIG. 1 illustrates a front view of the shoulder and waist harness for use with a wheelchair by itself;

FIG. 2 illustrates a back view of the shoulder and waist harness for use with a wheelchair by itself;

FIG. 3 illustrates a front view of the shoulder and waist harness for use with a wheelchair in which the front cover is open to reveal the connection of the front member and rear member forming the front cover;

FIG. 4 illustrates a perspective view of the front cover in an open position with the front member aligned adjacent the rear member.

DETAILED DESCRIPTION OF THE EMBODIMENT

Figure 5:
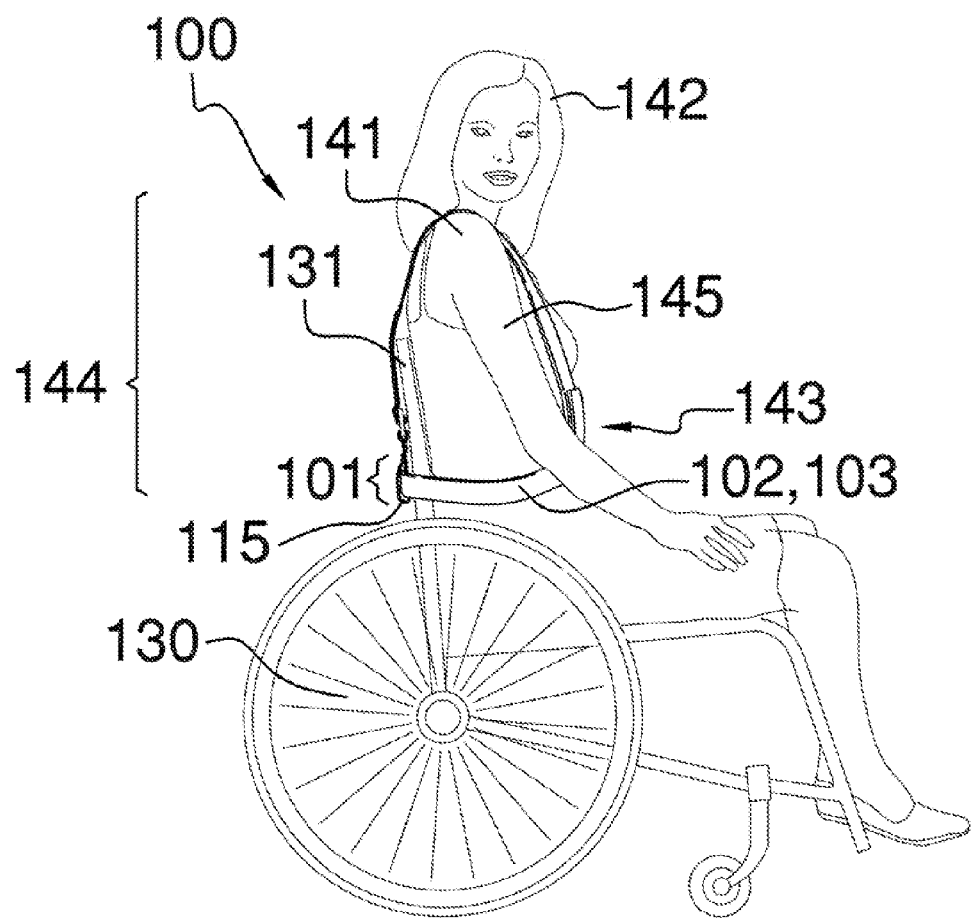
FIG. 5 illustrates a side view of the shoulder and waist harness for use with a wheelchair in use with an occupant seated in a wheelchair.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-5. A shoulder and waist harness for use with a wheelchair 100 (hereinafter invention) includes a horizontal belt 101 further defined by a first belt member 102 and a second belt member 103 each having first distal ends 104 and second distal ends 105. The first distal ends 104 of the first belt member 102 and the second belt member 103 include a buckle 106 that connects to secure the first belt member 102 to the second belt member 103 along a rear surface of a wheelchair 130. More specifically, the buckle 106 connects the first belt member 102 to the second belt member 103 at a rear surface of a seat back 131 of said wheelchair 130.

The second distal ends 105 of the first belt member 102 and the second belt member 103 are affixed to either a front 109 member or a rear member 110 forming a front cover 108. The invention 100 includes the front cover 108 in order to secure the first belt member 102 to the second belt member 103 of the horizontal belt 101. The front member 109 is further defined by a rear surface 111, whereas the rear member 110 includes a front surface 112. The front member 109 and the rear member 110 each include a corresponding nylon hook or loop strip 113 along the rear surface 111 and the front surface 112 so as to secure the front member 109 to the rear member 110.

The front member 109 of the front cover 108 also includes a lift tab 108', which aids in separating the front member 109 from the rear member 110.

The invention 100 includes shoulder straps 114 that attach to the horizontal belt 101 via shoulder strap loops 115 formed at a first distal end 116 of each shoulder strap 114. The shoulder strap loops 115 encircle the first belt member 102 or the second belt member 103, respectively. The shoulder straps 114 are designed to extend up from the rear of the wheelchair 130, which places the shoulder strap loops 115 adjacent to the buckle 106 connecting the first belt member 102 to the second belt member 103. The shoulder straps 114 extend vertically along the rear of the seat back 131 of the wheelchair 130, and over shoulders 141 of an occupant 142. The shoulder straps 114 include a second distal end 117 that is affixed to either the front member 109 or the rear member 110 of the front cover 108. The second distal end 117 connects to the front cover 108 in a manner consistent with the horizontal belt 101. Moreover, the front member 109 is affixed to the shoulder strap 114 and corresponding belt member 102/103, whereas the rear member 110 is affixed to an opposing shoulder strap 114 and corresponding belt member 103/102, respectively.

The front cover 108 is responsible for securing the shoulder straps 114 and the horizontal belt 101 to a belly 143 of the occupant 142. Moreover, the shoulder straps 114 work in conjunction with the horizontal belt 101 to secure the torso 144 to the seat back 131 of the wheelchair 130, and thereby preventing unintended or undesired falling of the end user 142 from the wheelchair 130 when occupying the wheelchair 130. The horizontal belt 101 is responsible for encircling both the seat back 131 of the wheelchair 130 and the belly 143 of the occupant 142. The shoulder straps 114 extend upwardly from behind the seat back 131 of the wheelchair 130 over the shoulders 141 of the occupant 142, and attaching to the front cover 108. It shall be noted that the invention 100 does not limit or restrict movement of arms 145 of the occupant 142.

The shoulder straps 114 include adjustment loops 119, which enable an overall length of the shoulder straps 114 to be adjusted in order to accommodate differently sized wheelchairs 130 and/or occupants 142. The horizontal belt 101 and the shoulder straps 114 include elastic strips 120, which provide stretching as needed in use. The elastic strips 120 are defined as the type of elastic fabric commonly used in clothing, and enables the horizontal belt 101 and the shoulder straps 114 to form fit to the particular use.

Both the horizontal belt 101 and the shoulder straps 114 are made of a flexible fabric or webbing that provides for bending around portions of the wheelchair 130 and/or occupant 142.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A shoulder and waist harness for use with a wheelchair comprising:
   a horizontal belt from which shoulder straps extend;
   wherein the horizontal belt is configured to encircle both the seat back of a wheelchair and a belly of an occupant, whereas the shoulder straps extend vertically from behind the seat back of the wheelchair, up and over shoulders of said occupant, before connecting to a front cover thereby securing a torso of said occupant to the seat back of the wheelchair without restriction or movement of arms of said occupant;
   wherein the horizontal belt is further defined by a first belt member and a second belt member each having first distal ends and second distal ends; wherein the first distal ends of the first belt member and the second belt member include a buckle that connects to secure the first belt member to the second belt member along said rear surface of a wheelchair;
   wherein the second distal ends of the first belt member and the second belt member are each affixed to either a front member or a rear member forming the front cover, and which connects to the form the front cover adjacent said belly of said occupant;
   wherein the front member includes a rear surface whereas the rear member includes a front surface; wherein the rear surface and the front surface each includes a nylon hook or loop strip in order to secure together;
   wherein the front cover also includes a lift tab on the front member, which aids in separating the nylon hook or loop strips of the front member with respect to the rear member.

2. The shoulder and waist harness for use with a wheelchair as described in claim 1 wherein the shoulder straps attach to the horizontal belt via shoulder strap loops formed at a first distal end of each shoulder strap; wherein the shoulder strap loops encircle the first belt member or the second belt member, respectively.

3. The shoulder and waist harness for use with a wheelchair as described in claim 1 wherein the shoulder straps include a second distal end that is affixed to either the front member or the rear member of the front cover.

4. The shoulder and waist harness for use with a wheelchair as described in claim 3 wherein the front member is affixed to one of the shoulder straps and the corresponding member of the horizontal belt while the rear member is affixed to an opposing shoulder strap and corresponding member of the horizontal belt.

5. The shoulder and waist harness for use with a wheelchair as described in claim 1 wherein the shoulder straps include adjustment loops, which enable an overall length of the shoulder straps to be adjusted in order to accommodate differently sized wheelchairs and/or occupants.

6. The shoulder and waist harness for use with a wheelchair as described in claim 1 wherein the horizontal belt and the shoulder straps include elastic strips, which provides stretching.

7. A shoulder and waist harness for use with a wheelchair comprising:
   a horizontal belt from which shoulder straps extend;
   wherein the horizontal belt is configured to encircle both the seat back of a wheelchair and a belly of an occupant, whereas the shoulder straps extend vertically from behind the seat back of the wheelchair, up and over shoulders of said occupant, before connecting to a front cover thereby securing a torso of said occupant to the seat back of the wheelchair without restriction or movement of arms of said occupant;

wherein the horizontal belt is further defined by a first belt member and a second belt member each having first distal ends and second distal ends; wherein the first distal ends of the first belt member and the second belt member include a buckle that connects to secure the first belt member to the second belt member along said rear surface of a wheelchair;

wherein the second distal ends of the first belt member and the second belt member are each affixed to either a front member or a rear member forming the front cover, and which connects to the form the front cover adjacent said belly of said occupant;

wherein the front member includes a rear surface whereas the rear member includes a front surface; wherein the rear surface and the front surface each includes a nylon hook or loop strip in order to secure together;

wherein the front cover also includes a lift tab on the front member, which aids in separating the nylon hook or loop strips of the front member with respect to the rear member.

8. The shoulder and waist harness for use with a wheelchair as described in claim 7 wherein the shoulder straps attach to the horizontal belt via shoulder strap loops formed at a first distal end of each shoulder strap; wherein the shoulder strap loops encircle the first belt member or the second belt member, respectively.

9. The shoulder and waist harness for use with a wheelchair as described in claim 8 wherein the shoulder straps include a second distal end that is affixed to either the front member or the rear member of the front cover.

10. The shoulder and waist harness for use with a wheelchair as described in claim 9 wherein the front member is affixed to one of the shoulder straps and the corresponding member of the horizontal belt while the rear member is affixed to an opposing shoulder strap and corresponding member of the horizontal belt.

11. The shoulder and waist harness for use with a wheelchair as described in claim 7 wherein the shoulder straps include adjustment loops, which enable an overall length of the shoulder straps to be adjusted in order to accommodate differently sized wheelchairs and/or occupants.

12. The shoulder and waist harness for use with a wheelchair as described in claim 7 wherein the horizontal belt and the shoulder straps include elastic strips, which provides stretching.

* * * * *